(12) United States Patent
Gavriely

(10) Patent No.: US 7,854,748 B2
(45) Date of Patent: Dec. 21, 2010

(54) DEVICE AND METHOD FOR EXCLUDING BLOOD OUT OF A LIMB

(76) Inventor: Oren Gavriely, 116A Moriah Ave., Haifa (IL) 34618

( * ) Notice: Subject to any disclaimer, the term of this patent is extended or adjusted under 35 U.S.C. 154(b) by 1174 days.

(21) Appl. No.: 10/498,369

(22) PCT Filed: Dec. 9, 2002

(86) PCT No.: PCT/IL02/00992

§ 371 (c)(1),
(2), (4) Date: Dec. 7, 2004

(87) PCT Pub. No.: WO03/049623

PCT Pub. Date: Jun. 19, 2003

(65) Prior Publication Data

US 2005/0080450 A1    Apr. 14, 2005

(51) Int. Cl.
*A61B 17/00* (2006.01)
(52) U.S. Cl. .................................. 606/203
(58) Field of Classification Search ............... 606/201, 606/202, 203, 204; 223/111, 112; 602/63
See application file for complete search history.

(56) References Cited

U.S. PATENT DOCUMENTS

| | | | | |
|---|---|---|---|---|
| 800,467 A * | 9/1905 | Myers | ............ | 602/5 |
| 814,795 A * | 3/1906 | Myers | ............ | 602/6 |
| 2,149,149 A * | 2/1939 | Scheinberg | ............ | 450/111 |
| 2,320,179 A * | 5/1943 | Gray | ............ | 600/499 |
| 2,333,237 A * | 11/1943 | Erekson | ............ | 606/203 |
| 2,574,873 A * | 11/1951 | Jobst | ............ | 602/63 |
| 2,582,648 A * | 1/1952 | Mowbray | ............ | 36/8.1 |
| 2,796,207 A * | 6/1957 | Young | ............ | 223/111 |
| 3,097,644 A * | 7/1963 | Parker | ............ | 602/79 |
| 3,227,335 A * | 1/1966 | Minnema et al. | ............ | 223/111 |
| 3,279,459 A * | 10/1966 | Schenker | ............ | 600/499 |
| 3,454,010 A * | 7/1969 | Miller et al. | ............ | 606/202 |
| 4,566,436 A * | 1/1986 | Loefqvist | ............ | 128/898 |
| 4,577,622 A * | 3/1986 | Jennings | ............ | 601/134 |
| 4,637,394 A * | 1/1987 | Racz et al. | ............ | 606/202 |
| 4,738,249 A * | 4/1988 | Linman et al. | ............ | 601/152 |
| 4,765,520 A * | 8/1988 | Barton | ............ | 223/111 |
| 4,848,324 A * | 7/1989 | Gavriely | ............ | 601/134 |
| 4,872,463 A * | 10/1989 | Nishizono | ............ | 128/844 |
| 4,972,850 A * | 11/1990 | Broad, Jr. | ............ | 128/844 |
| 5,163,448 A * | 11/1992 | Foldesy | ............ | 128/844 |
| 5,304,202 A * | 4/1994 | Stahl | ............ | 606/203 |
| 5,351,698 A * | 10/1994 | Wheeler et al. | ............ | 128/844 |
| 5,376,067 A * | 12/1994 | Daneshvar | ............ | 602/58 |
| 5,383,893 A * | 1/1995 | Daneshvar | ............ | 606/201 |
| 5,411,518 A * | 5/1995 | Goldstein et al. | ............ | 606/202 |
| 5,606,982 A * | 3/1997 | Piotti | ............ | 128/842 |
| 5,607,448 A * | 3/1997 | Stahl et al. | ............ | 606/203 |
| 5,620,001 A * | 4/1997 | Byrd et al. | ............ | 606/202 |
| 5,669,390 A * | 9/1997 | McCormick et al. | ............ | 600/499 |
| 5,695,520 A * | 12/1997 | Bruckner et al. | ............ | 606/204 |
| 5,876,436 A * | 3/1999 | Vanney et al. | ............ | 623/2.39 |

(Continued)

*Primary Examiner*—Darwin P Erezo
(74) *Attorney, Agent, or Firm*—Dvorah Graeser

(57) ABSTRACT

A device for applying pressure in progression to restrict the blood content of a limb, whereby at least an elastic tight sleeve is unfolded directionally on that limb towards the center of the body. The unfolding is streamlined using at least one auxiliary application strap. In certain embodiments a constricting toroid is used as a major restriction agent.

24 Claims, 3 Drawing Sheets

U.S. PATENT DOCUMENTS 5,893,871 A * 4/1999 Tanaka ................. 606/204
6,361,496 B1 * 3/2002 Zikorus et al. ............. 600/437
2005/0087573 A1 * 4/2005 Unsworth et al. ........... 223/112

* cited by examiner

DEVICE AND METHOD FOR EXCLUDING BLOOD OUT OF A LIMB

TECHNICAL FIELD OF THE INVENTION

The present invention relates generally to medical devices. More particularly the invention is in the fields of ambulatory medicine and to blood management in surgery.

BACKGROUND OF THE INVENTION

Haemodynamic shock continues to be a frequent cause of severe morbidity and mortality. Insufficient blood supply to the essential organs: the brain, heart, kidneys and the digestive system causes organ failure with rapid functional deterioration and, if not treated, irreversible damage. Shock is caused by either reduction of blood volume, or by inappropriate dilatation of the blood vessels. The result of both conditions is a discrepancy between the blood volume and the vascular volume, leading to a fall in blood flow and pressure. The ultimate treatment of shock is directed toward restoring normal blood volume-vascular volume relationship. This treatment usually requires care by skilled medical personnel in an appropriately equipped facility. These therapeutic measures can only be successful if irreversible damage to the essential organs has been prevented during the time from the onset of shock. This can be achieved by diverting blood and directing blood flow away from the tissues that can withstand prolonged lack of blood supply such as the muscles, bones and skin to the essential organs.

Blood diversion is also applied frequently by orthopedic surgeons during operative procedures on the legs and arms. This is achieved by applying a tight bandage to a limb that is to be operated on and then by inflating a pneumatic cuff to a pressure of approximately 250 mm Hg at the proximal end of the limb to create a 'bloodless' surgical field.

Another aspect of blood diversion is the use of tight support stockings, support hoses, or elastic sleeves to prevent undesired pooling of blood in the veins (normal and varicose) of the lower extremities. This application is focused at limiting the volume of the deep and superficial veins, which may cause venous stasis of blood resulting in intra-vascular clotting leading to superficial or deep-vein thrombosis. The pressure needed to compress the veins is substantially lower than that needed for arterial draining and blocking and ranges from 20 to 60 mm of Hg. Likewise, it is often desired to apply to an ailing, injured or burned limb a tight tubular elastic bandage that is coated with a medicated cream, jelly or ointment for treatment of the injury, skin illness or burn. This tubular bandage must be in tight contact with the skin surface for best clinical results of the treatment.

The treatment for shock disclosed in U.S. Pat. No. 4,848,324 includes an elastic long sleeve that is rolled upon itself to create a toroidal compressive ring that may be rolled up onto a limb to displace its blood toward the central circulation.

SHORT DESCRIPTION OF THE DRAWINGS

DESCRIPTION OF THE INVENTION AND BEST MODES FOR ITS IMPELEMENTATION

One implementation of a device of the invention is in the emergency treatment of shock through shifting of blood and directing the cardiac output away from the limbs into the circulation of the center of the body. Another typical implementation is in limb surgery, where it is used during operative procedures to create a 'bloodless' surgical field. For this use, the device provides a potentially clean and sterile environment, and is adaptable to limbs of various sizes. Such a task is performed by excluding blood from the limb, as will be described further on.

Figure 1:
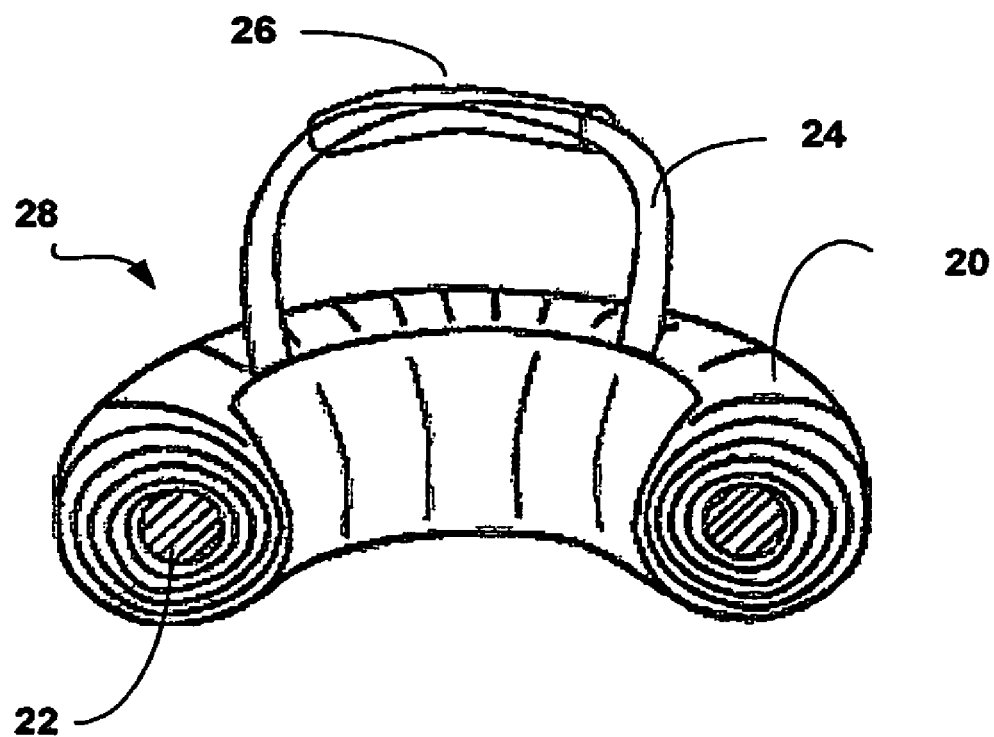
FIG. 1 is a sectional view of a device of the invention, showing one of the application handles and straps.

The general structure of a preferred embodiment of the invention is described in FIG. 1 to which reference is now made, shows a cross section in an elastic tight sleeve 20 folded around an elastic ring-like structure 22, along with one of the auxiliary application straps 24 and one of the strap pulling handles 26. The ring-like structure, hereinafter named a constricting toroid, acts as a major compressive element by generating the force that is required to overcome the arterial, capillary and venous blood pressure in the limb. The elastic sleeve 20 is made from an elastic material such as the Tubigrip® of ConvaTec, USA. Employed together, the elastic constricting toroid and the folded sleeve form a thick elastic constricting annulus (ECA) 28. The pressure that is exerted by the ECA on the limb is higher than the one that would have been exerted by constricting toroid structure alone, due to the added compression of the elastic sleeve wrapped around, and because the reduced inner diameter of the annulus with the sleeve. Decreasing the diameter of the opening or/and the compliance of the constricting toroid or/and the sleeve material increases the constricting pressure exerted on the limb, by the annulus of the invention.

The auxiliary application straps 24 and an associated handle 26 thereof are used a means of streamlining the application of the ECA to the limb. The strap 24 and typically at least another one, not shown, are wrapped around the ring alongside the elastic sleeve 20. When the handles 26 are pulled, the ECA is rolled up the limb as the elastic sleeve 20 is being unfolded. Optional auxiliary removal straps (not shown) may be placed beneath the elastic sleeve 20 so that when they are pulled the annulus rolls down the limb and the elastic sleeve 20 gets re-wrapped around ring 22. All the straps are typically made of a thin yet strong fabric.

Figure 2:
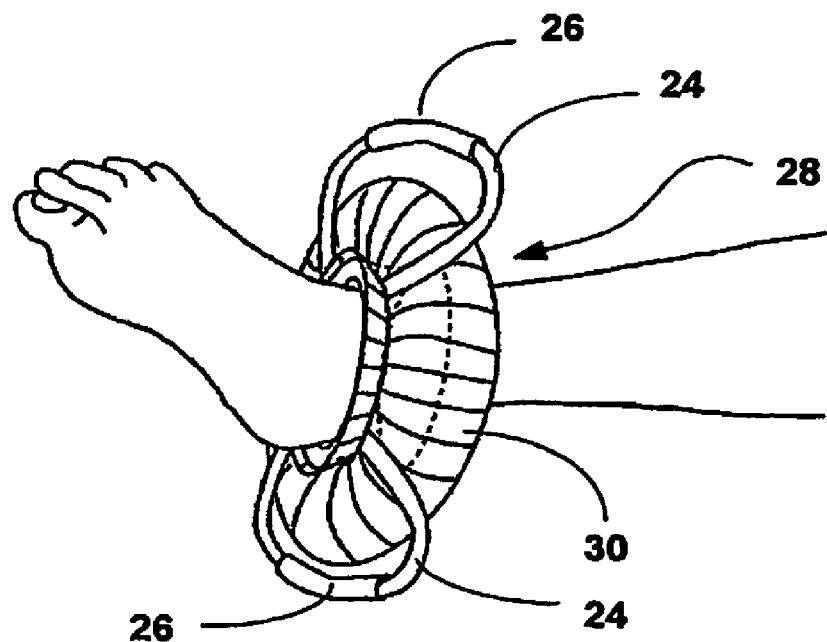
FIG. 2 is a schematic view of a device of the invention including an optional rigid application ring.

An auxiliary application ring is optional in a preferred embodiment of the present invention. As shown in FIG. 2, to which reference is now made, the ECA 28 is shown passed over the ankle/wrist. In this position, the application straps 24 can be pulled by the handles 26 along the limb. To apply the ECA, initially it is dismounted from the rigid application ring 30 onto the limb. Then as the application straps 24 are pulled further up the limb, the ECA is rolled up along the limb while gradually unfolding the elastic tight sleeve. While the ECA is rolled up, the constricting toroid and the winded remainder of the elastic sleeve 20 constantly exert on the limb pressure that is higher than the arterial, capillary and venous blood pressure. This pressure squeezes the limb in progression from a distal position to a more proximal position, causing blood to flow out of the limb thereby and transfusing it to the vital organs, thereupon raising the patient's blood pressure. The constrictive pressure generated by the ECA is higher than the arterial blood pressure yet lower than the pressure that may cause crush injury to the tissues beneath it.

Figure 3:
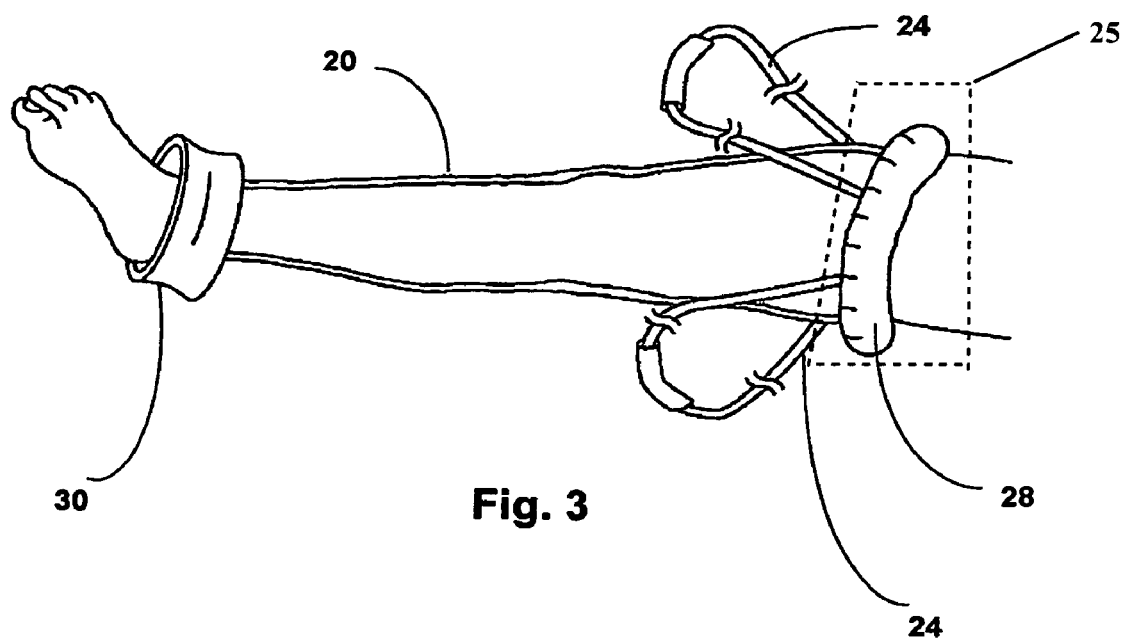
FIG. 3 is a side view of a rolled-up sleeve on a lower limb of a person.

As described in FIG. 3, to which reference is now made, the ECA 28 is rolled up the patient's leg. The application ring 30 remains at the ankle level and can be easily removed and discarded. The elastic sleeve 20 tightly covers the limb and pressurizes it, but can also be cut away and discarded, if access to the skin surface is required for medical treatment or for other reasons, because the constrictive pressure exerted by the ECA 28, which includes in this configuration the constricting toroid and the remainder of the wound elastic sleeve, is unaffected by such action. The constrictive pressure applied by the ECA is the major blood restrictive element in this embodiment of the invention, completely stopping the flow of blood into the limb. In such application cases as the ECA is fully deployed on the limb leaving no unwound elastic sleeve, the ECA is comprised essentially of the constricting toroid which prevents the blood from reentering the limb.

The application straps 24 are extended at this configuration. An additional set of two straps made from strong thin fabric, not shown, are at this configuration rolled around the remainder of the unrolled ECA, to assist in the removal of the ECA from the patient. The role of the rigid application ring 30 is in assisting to quickly bring the relatively thick ECA, at the unfolded configuration, over wider dimensions of the heel or palm of the hand. The application element typically has an oval shape with a concave profile that supports the ECA and prevents the ring from slipping off it. The application ring is made of a slightly flexible material such as plastic resin.

The ECA can be made in different sizes to fit large and small individuals. In addition, there may be produced two size categories to fit lower or upper limbs respectively. Versatility is increased by the fact that the size designated for an adult upper limb may be applied to the lower limb of a child.

Constricting Toroid Structure

The constricting toroid of the invention, may assume any one of several forms. A homogenous cross-section constricting toroid made of a single homogenous solid ring, is the simplest form. Although such a constricting toroid, when appropriately applied, performs its function of retaining blood, its deployment requires substantial physical strength and dexterity, especially when speed is an issue of concern. In addition, generally a larger area of contact between the elastic element of the ECA and the human body surface is preferred. This is because the pressure that is generated by a wider ring is distributed over a larger area causing less local pain and a lesser risk of damage to the underlying tissues. Furthermore, the improved grip on a thicker ring makes it easier to advance it up the limb. However, if the ring is circular, revolving around itself as it rolls up the limb the, requires more muscle force is required for the application the larger it grows.

Figure 4:
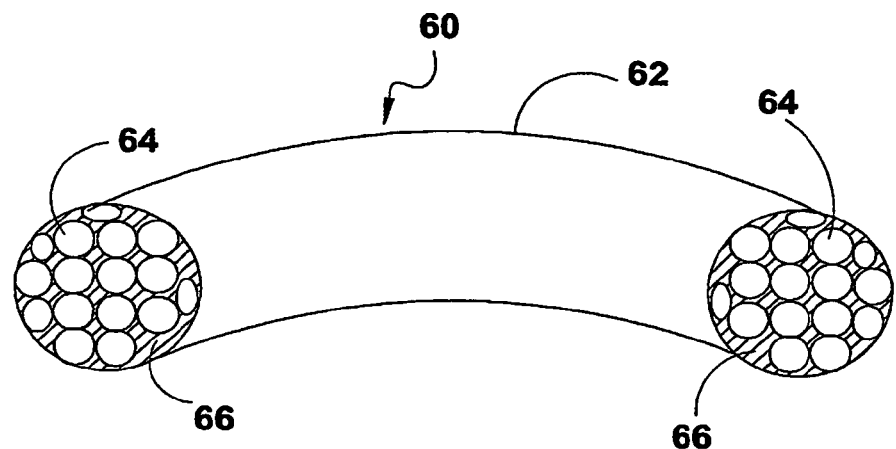
FIG. 4 is a sectional view of the toroidal ring construction comprising a tubular toroid containing a multiplicity of lubricated solid toroids.
Figure 5:
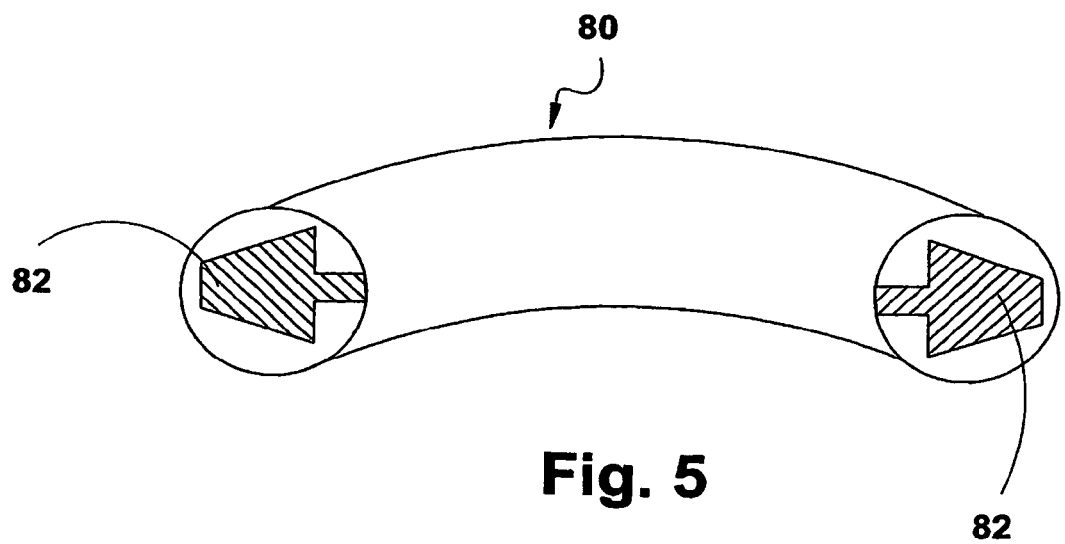
FIG. 5 is a sectional view of a toroidal structure in accordance with the invention containing an internal void.

In FIGS. 4-5 other forms of the constricting toroid are shown that may be used to achieve the desired effect with a greater ease of application. In FIG. 4 a cross sectional view of an elastic constricting toroid 60 is shown, comprising a flexible toroidal tube 62 that contains inner rings such as ring 64 in its void volume. The included one or more rings are typically homogenous. Another optional aspect of such an embodiment is a lubrication fluid. Between the elastic included rings and the flexible toroidal tube 62 there is disposed a lubrication fluid, filling completely or partially the hatched space designated 66. This lubricant reduces the friction between the toroidal tube 62 and the inner elastic rings. When the toroidal tube 62 is rolled up the limb, it rotates around its own axis, while the internal elastic rings slide up the limb without substantially rotating.

In FIG. 5 to which reference is now made, another preferred embodiment of the constricting toroid is described. In this example, a thick wall elastic tubular torus 80 spreads wider as it is being rolled up the limb, as compared to a solid monolithic torus. The wider torus enables better grip of the device and distributes the pressure on a wider area of the skin surface. The void volume 82, marked hatched, of the elastic torus is filled with granular or dense liquid filling. The filling material enlarges the elastic ring's thickness and prevents the tube from collapsing. The advantage of this design is that less force is required to roll this elastic ring around its own axis than a ring that is completely solidly filled. The elastic tubular toroid may be made from elastic materials such as silicone or rubber or may be supported internally by twisted, bent or coiled metal or wire (spring), which returns to its shape or position after being stretched or compressed.

The modular device of the invention containing separate elements, an elastic O-ring and a separate sleeve allow flexibility of materials and material properties that promote the economy of manufacturing, and obviate the need for use of allergy-causing latex. In the instant invention there is a distinct separation between the sleeve, whose role is largely that of a geometric spacer and the elastic ring, which generates the bulk of the constrictive compression force. This modular approach facilitates the use of a device with a non-circular cross section and control the contact area on the body surface. In embodiments of the invention employing an application ring, application straps and pulling handles, the application of the device to a limb is streamlined, and can be very quick. A securing girdle 25 is an additional appliance which can be applied around the limb, preventing inadvertent dislocation of the ECA.

The invention can be implemented without the elastic constricting toroid. Using the pulling straps for unfolding and tightly applying a tubular pre-folded elastic tight sleeve, such as a stockings or hose of the prior art, promotes the quick and even application of such elastic tight sleeve to individuals who will have developed complications of venous stasis during prolonged standing or sitting, such as during long flights. Such a elastic tight sleeve or hose is typically conical in shape or contoured to the shape of the leg to effect uniform distribution of the compression pressure. Another aspect of this invention is a pre-folded tight sleeve including a medicament, pre-coated or pre-absorbed with medicated cream, jelly or ointment. Such an elastic tight sleeve can be rapidly and easily applied to a patient's limb by pulling the pulling straps towards the trunk.

The invention claimed is:

1. A device for constricting a limb whereby the blood content of said limb is restricted, said device comprising: a constricting toroid; an elastic tight sleeve folded around said constricting toroid, wherein said elastic tight sleeve is separate from said constricting toroid; and at least one auxiliary strap connected to said constricting toroid at least two separate points, wherein upon pulling said at least one auxiliary strap, said constricting toroid and said elastic tight sleeve are applied to said limb by rolling onto distal end of said limb and rolling up said limb to a proximal location of said limb.

2. A device as in claim 1 and wherein said sleeve contains a medicament.

3. A device as in claim 1 wherein said at least one auxiliary strap comprises an additional removal strap.

4. A device as in claim 1 wherein said auxiliary strap has an associated handle attached.

5. A device as in claim 4, wherein said auxiliary strap forms a loop and said handle is at a center of said loop.

6. A device as in claim 1 wherein said constricting toroid is a single homogeneous solid ring.

7. A device as in claim 1 and wherein said constricting toroid is tubular.

8. A device as in claim 7 and wherein said constricting toroid contains inner rings within said single void volume.

9. A device as in claim 1 and wherein said constricting toroid contains a single void volume.

10. A device as in claim 9 and wherein said void volume is at least partially filled with a lubricant.

11. A device as in claim 1, wherein said at least one auxiliary strap is adapted to unroll as said constricting toroid is rolled on said limb.

12. A device as in claim 1, wherein said elastic tight sleeve is windable on said elastic constricting toroid, and said elastic tight sleeve and said elastic constricting toroid form an elastic constructive annulus having an inner diameter for constricting said limb.

13. A device as in claim 12, wherein said inner diameter of said elastic constrictive annulus increases as said tight elastic sleeve gradually unfolds up said limb, and wherein an inner diameter is at all times small enough to keep said constriction at an applied pressure higher than the arterial blood pressure of said limb.

14. A device as in claim 13, wherein said elastic constricting toroid exerts pressure higher than the arterial blood pressure of said limb in at least in a proximal position on said limb.

15. A device as in claim 1, wherein said at least one auxiliary strap is looped to have two ends connected to said constricting toroid at separate points.

16. A device as in claim 1, wherein said at least one auxiliary strap comprises a first narrow auxiliary strap connected to said constricting toroid at two separate points and a second narrow auxiliary strap connected to said constricting toroid at two separate points.

17. A kit for constricting a limb, said kit comprising a device according to claim 1 and a safety girdle only applied around the limb for preventing inadvertent dislocation of said constricting toroid.

18. A method for restricting the blood content of a limb, comprising rolling a constricting toroid directionally on said limb from an extremity of said limb towards the center of the body for pressurizing said limb in progression from its distal end towards its proximal end, said constricting toroid having a separate elastic tight sleeve folded around it, wherein said elastic tight sleeve folded around said constricting toroid is unfolded directionally on said limb towards the center of the body as said constricting toroid is rolled on said limb, and whereby said rolling is performed by applying a substantive amount of pulling force on at least one auxiliary application strap connected to said constricting toroid at least two separate points.

19. A device for constricting a limb whereby the blood content of said limb is restricted, said device comprising:
an elastic sleeve;
at least one constricting means for applying to said limb by rolling, said at least one constricting means further comprising a toroid as a major compressive element, wherein said toroid is selected from the group consisting of a solid ring and a ring-shaped tube, and wherein said elastic sleeve is wrapped around but is physically separate from said toroid;
and at least one auxiliary strap connected to said constricting means, wherein upon pulling said at least one auxiliary strap, said toroid and said elastic sleeve are applied to said limb by rolling onto distal end of said limb and rolling up said limb to a proximal location of said limb.

20. The device of claim 19, wherein said toroid is a single homogeneous solid ring.

21. A device for constricting a limb whereby the blood content of said limb is restricted, said device comprising:
an elastic sleeve;
at least one constricting means for applying to said limb by rolling, said at least one constricting means further comprising a toroid as a major compressive element, wherein said toroid comprises at least one of a plurality of solid inner rings or a plurality of tubular inner rings, and wherein said elastic sleeve is wrapped around but is physically separate from said toroid; and
at least one auxiliary strap connected to said constricting means, wherein upon pulling said at least one auxiliary strap, said toroid and said elastic sleeve are applied to said limb by rolling onto distal end of said limb and rolling up said limb to a proximal location of said limb.

22. The device of claim 21, wherein said toroid comprises a ring-shaped tube and wherein said plurality of solid inner rings are contained within said ring-shaped tube, such that said solid inner rings slide up said limb without rotation.

23. The device of claim 22, further comprising a lubricant present in a void volume of said ring-shaped tube between said solid inner rings and said ring-shaped tube.

24. A device for constricting a limb whereby the blood content of said limb is restricted, said device comprising: a continuous and uniform constricting toroid; an elastic tight sleeve folded around said constricting toroid, wherein said elastic tight sleeve is separate from said constricting toroid; and at least one auxiliary strap connected to said constricting toroid at least two separate points, wherein upon pulling said at least one auxiliary strap, said constricting toroid and said elastic tight sleeve are applied to said limb by rolling onto distal end of said limb and rolling up said limb to a proximal location of said limb.

* * * * *